United States Patent

Jones

Patent Number: 5,919,734
Date of Patent: Jul. 6, 1999

[54] OIL-BASED FATTY ACID HERBICIDAL COMPOSITION AND METHOD OF APPLYING FATTY ACID HERBICIDES

[75] Inventor: Keith Jones, San Diego, Calif.

[73] Assignee: Mycogen Corporation, San Diego, Calif.

[21] Appl. No.: 08/839,187

[22] Filed: Apr. 22, 1997

Related U.S. Application Data

[60] Provisional application No. 60/016,019, Apr. 23, 1996, abandoned.

[51] Int. Cl.⁶ ............ A01N 37/02
[52] U.S. Cl. ............ 504/320
[58] Field of Search ............ 504/320

[56] References Cited

U.S. PATENT DOCUMENTS 4,975,110  12/1990  Puritch et al. ............ 71/113
5,098,468   3/1992  Puritch et al. ............ 71/113

*Primary Examiner*—S. Mark Clardy
*Attorney, Agent, or Firm*—Saliwanchik, Lloyd & Saliwanchik

[57] ABSTRACT

Fatty acid herbicides are applied in an oil based formulation without dilution in water. The application volume rate is low, ie., 25 gallons/acre or less, which saves time, energy and other resources. Less fatty acid herbicide is also employed for equivalent control using high volume water based formulations.

10 Claims, 1 Drawing Sheet

OIL-BASED FATTY ACID HERBICIDAL COMPOSITION AND METHOD OF APPLYING FATTY ACID HERBICIDES

This application claims benefit of priority to Provisional Application Ser. No. 60/016,019, filed Apr. 23, 1996, abandoned.

BACKGROUND OF THE INVENTION

The present invention relates to a method of applying fatty acid herbicides and to oil-based fatty acid herbicidal compositions. The present compositions are more biologically active and small volumes can be employed for control of unwanted vegetation. The herbicidal compositions are applied without aqueous dilution.

Fatty acid herbicides are well known in the art and are generally considered to be environmentally friendly. Fatty acid herbicides are typically supplied as concentrates that are diluted with water and applied as an oil-in-water emulsion. These concentrates usually contain the fatty acid active ingredient and emulsifying agents including surfactants and oils. Application rates vary but usually the fatty acid emulsions are applied at application rates of at least 50–100 gallons or more per acre and deliver the active fatty acid herbicide at concentrations of 1–8% by weight.

U.S. Pat. Nos. 4,975,110; 5,106,410 and 5,098,467 disclose fatty acid herbicidal compositions that contain C8–12 fatty acids, a surfactant and water with pelargonic acid being a preferred fatty acid herbicide. U.S. Pat. Nos. 5,098,468 and 5,035,741 also disclose fatty acid herbicidal compositions that contain C8–12 carbon fatty acids, an oil component, an emulsifier and water. Single phase concentrates are disclosed in U.S. Pat. Nos. 5,098,468 and 5,035,741 that contain the fatty acid(s), oil and emulsifier. The concentrate is diluted with water to form a ready to use composition containing 1–8% by weight fatty acid which is applied at a rate of 8–200 gallons/acre.

Fatty acid herbicides include fatty acid esters of $C_6$–$C_{20}$ monocarboxylic acids such as those disclosed in U.S. Pat. No. 5,284,819. Additionally, fatty acid salts such as those disclosed in USSN 08/458,546 and U.S. Pat. Nos. 2,626,862; 4,975,110; and 5,035,741, can be employed as fatty acid herbicides.

BRIEF SUMMARY OF THE INVENTION

Briefly, in accordance with the present invention, fatty acid herbicides are combined with an effective amount of an oil for application to unwanted vegetation. No water is employed in the application which provides an advantage of applying small volumes to crops. Application of substantially smaller volumes saves energy, time and other resources. Overall, less fatty acid herbicide is required for equivalent control of water based formulations which must contain more fatty acid herbicide. Fatty acid herbicides include C8–C12 monocarboxylic fatty acids. Pelargonic acid is a preferred fatty acid herbicide. Oils are any oil that is physically compatible with the fatty acid herbicide. Preferred oils are vegetable oils, terpenoid based oils and paraffinic mineral oils (crop oils).

Of particular interest in the practice of the present invention, pelargonic acid is mixed with a crop oil (11 N Oil) and applied to crops at a rate of 3–10 gallons/acre. The concentration of pelargonic acid is 15–85% by weight of the formulation.

DETAILED DISCLOSURE OF THE INVENTION

Figure 1:
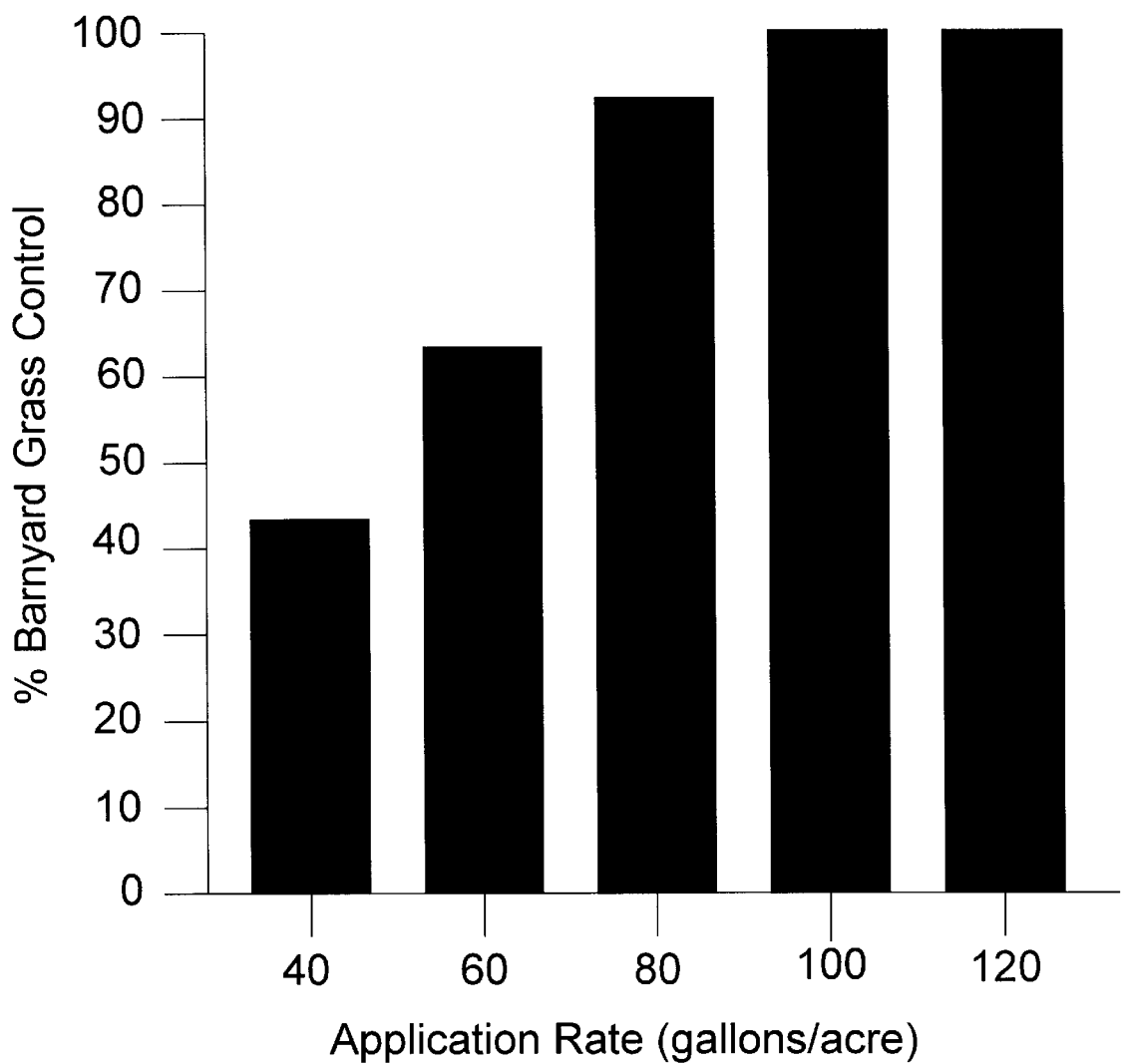
FIG. 1 is a bar graph depicting the effect of carrier volume on efficacy of SCYTHE pelargonic acid (gallons/acre) in the control of barnyard grass.

In practicing the present invention, one or more fatty acid herbicides are combined or mixed with one or more oils that are physically compatible with the fatty acid herbicides. The fatty acid herbicide/oil composition is applied directly to unwanted vegetation at volumes that are substantially smaller than water based systems for applying fatty acid herbicides. Typically, the present fatty acid/oil compositions are applied at rates of less than 25 gallons/acre and preferably at a rate of from about 3–10 gallons/acre.

The fatty acid component of the herbicidal composition of this invention comprises any herbicidal fatty acid including one or a mixture of alpha monocarboxylic fatty acids having a hydrocarbon chain between 6 and 20, and preferably between 8 and 12 carbon atoms. The fatty acid herbicide can be a free fatty acid, or a salt, or ester thereof. Preferred fatty acid salts include aliphatic amine salts of fatty acid herbicides disclosed in co-pending USSN 08/458,546 which is incorporated herein by reference. Isopropylamine salts of pelargonic acid are particularly preferred. Preferred fatty acid esters include those ester disclosed in U.S. Pat. No. 5,284,819 which is incorporated herein by reference. Monoglycol esters of $C_6$–$C_{13}$ fatty acids are particularly preferred.

In one embodiment, the fatty acid is pelargonic acid, which may be used alone or as the major constituent (ie., about 90%) of a mixture which includes other fatty acids. In another preferred embodiment the fatty acid component comprises a mixture of pelargonic acid, caprylic and capric acids wherein pelargonic acid accounts for most of the mixture and caprylic and capric acids are present in relatively small amounts. Such a mixture, having about 94% pelargonic acid, 4% caprylic acid and 2% capric acid is commercially available under the trademark "EMERY 1202" from Emery Division. Quantum Chemical Corporation, Cincinnati, Ohio. In another embodiment, pelargonic acid may be combined with undecanoic acid and this combination utilized as the active ingredients of the herbicidal composition.

The fatty acid components set forth above are examples of currently preferred fatty acids and fatty acid mixtures. It is expected that the ratios of the various constituents of these fatty acids and mixtures may be altered or that other combinations of fatty acids having between 6 and 20 carbon atoms may be used to obtain the same or better results. Preferably, the active ingredient is an unsaponified single fatty acid or a mixture of unsaponified fatty acids.

The oil component of the present invention preferably is a terpenoid, a triglyceride, or a mineral oil. The terpenoid-based oils which may be used with this invention include pine oil, eucalyptus oil, orange oil, cedar oil and the like. Useful triglycerides include various vegetable oils such as cottonseed oil, linseed oil, coconut oil, various grades of soybean oil (e.g., crude soybean oil, degummed soybean oil, salad grade soybean oil), sunflower oil, olive oil, grape oil, rapeseed oil and mustard oil. Cottonseed oil is currently the most preferred triglyceride. The mineral oils which may be used with the herbicidal formulation of this invention are refined horticultural oils such as paraffinic, natural petroleum distillates. An example of a preferred mineral oil is commercially available under the trademarks "SUNSPRAY 6E," "SUNSPRAY 6N" and 'SUNSPRAY 6E PLUS" from Sun Refining and Marketing Company of Philadelphia, Pa. Such a product contains about 99% refined petroleum distillates and about 1% emulsifier.

Cottonseed oil is the most preferred oil component for use with the present herbicidal formulation due to its low toxicity to humans and animals, its environmental compatibility and also because the phytotoxicity of the compositions which contain it. Pine, olive and sunflower oils each may be effectively used in herbicidal compositions to provide similar levels of phytotoxicity. However, factors such as high cost, strong odor, or both, render such oils less favorable than cottonseed oil. It is understood that other triglycerides or terpenoid-based oils may be effectively used in a herbicidal formulation falling within the scope of this invention. Moreover, mineral oils may be used in such a herbicidal formulation with equal or superior herbicidal characteristics to a formulation utilizing cottonseed oil.

The present oil based fatty acid formulation will contain at least about 10% by weight oil and typically at least about 50% by weight. When pelargonic acid is the fatty acid herbicide it is preferred to employ about 20% by weight oil and about 80% by weight pelargonic acid.

The present herbicidal composition may be prepared through a variety of known formulation and mixing techniques well known to the art. One preferred formulation technique involves charging a stainless steel or high density polyethylene tank, equipped with a paddle stirrer, with the desired amount of the oil component and to commence high speed paddle stirring at approximately 150 rpm. The fatty acid component is then added while stirring is continued for about 15 minutes.

The present formulation is a foliar applied, non-selective herbicide which may be sprayed upon unwanted weeds and grasses. The composition is most effective against young, succulent and actively growing weeds less than five inches in height. Several applications of the composition may be necessary to control certain grasses and established weeds. Maturing (flowering) and woody weeds are less susceptible to the formulation. Repeated applications of the composition may be necessary to kill perennial weeds.

Examples of annual weeds controllable by this herbicidal composition include Lambsquarter, Pigweed, Mustard, Shepherd's purse, Spiney annual sowthistle, Pineapple weed, Scentless mayweed, Wild buckwheat, Green foxtail, Stinkweed, Corn spurry, Common groundsel, Red sheep sorrel, Common chickweed, Wild radish, Common purslane, Whitestem filaree, Little mallow, Volunteer oat, False flax and Barnyard grass.

Examples of perennial weeds controllable by this herbicidal composition include Spotted catsear, True dandelion, Narrow-leaf plantain, Curled dock, Horsetail, Mouse-eared chickweed, Lupine, Clovers, Perennial ryegrass, Thistles and Quackgrass.

The herbicidal formulation of this invention may be applied by conventional spraying means. The formulation is most effective when applied to thoroughly cover all of the plant foliage. Most succulent annual weeds and grasses 5" or less in height, and top kill of perennials can be controlled with a spray volume of 3–5 gallons/acre. Larger annual weeds, weeds in dense stands, and more difficult to control perennials may require a spray volume in the range of 5–10 gallons or more/acre.

The fatty acid/oil compositions of the present invention are not only easier to apply, but the fatty acid herbicidal activity is actually enhanced when compared to application of the fatty herbicide when applied in a water based high volume (>50 gallons/acre) application. As can be seen in the following examples, low volume oil-based pelargonic acid provides better weed control than water based application of the same amount of pelargonic acid.

The present invention has the additional advantage of allowing for aerial application of fatty acid herbicides.

Aerial applicators usually prefer application volumes of 2–10 gallons/acre. As can be seen from FIG. 1, the fatty acid herbicides need high application volumes when water is employed as the carrier, usually in the 80–120 gallon/acre range. Reduced application volumes with a water carrier result in reduced activity of the fatty acid herbicide which can also be seen in FIG. 1. Additionally, many agronomic situations and applicators cannot handle high volume applications. Preferred application volumes are often in the 5–10 gallons/acre. Efficacy of the fatty acid herbicide is maintained at a much higher level when low carrier volumes utilize oil instead of water as the carrier.

The following examples illustrate the practice of the present invention and should not be construed as limiting its scope.

EXAMPLE 1

Oil Based Fatty Acid Herbicide Composition

Sicklepod, velvetleaf, yellow nutsedge, green foxtail and bindweed were grown in a greenhouse for 8 days. 2+ true leaves were on each plant. The plants were removed from the greenhouse and placed outside in San Diego, Calif. The plants were treated in a tracksprayer with various Sun 11 N Oil/pelargonic acid formulations listed below at full speed, ~6 mph, 45 psi, 8001 EVS nozzle.

| Formulation Number | 11 N Oil (wt %) | Pelargonic Acid (wt %) |
|---|---|---|
| 1 | 75% | 25% |
| 2 | 87.5 | 12.5 |
| 3 | 93.7 | 6.3 |
| 4 | 96.9 | 3.1 |

The plants were sprayed at 2:30pm and then 7:00am the following morning. The plants were rated 24 hours after the second treatment and then one week after the second treatment. The plants were rated on a scale of 0–10 with 0=no damage and 10=plant completely dead (wilted over). The average damage for each treatment is listed below:

| Plant | Formulation 1 | Formulation 2 | Formulation 3 | Formulation 4 |
|---|---|---|---|---|
| Sicklepod | 6.8 | 1.5 | 0.25 | 0 |
| Velvetleaf | 7.3 | 2.5 | 0 | 0 |
| Foxtail | 6.8 | 2.5 | 1 | 0 |
| Nutsedge | 0 | 0 | 0 | 0 |
| Bindweed | 7.5 | 2.3 | .25 | 0 |

EXAMPLE 2

Field Test

A field test was conducted that compared the fatty acid/oil formulations of the present invention with water based oil-in-water fatty acid emulsions and neat fatty acid. The formulations are listed below along with the volume application rate in gallons/acre.

| Treatment Number and Components (Formulation) | Application Rate (gal/acre) | Weight Percent of SCYTHE |
|---|---|---|
| 1. SCYTHE Pelargonic Acid (water) | 100 | 8% |
| 2. SCYTHE Pelargonic Acid (water) | 100 | 4% |

-continued

| Treatment Number and Components (Formulation) | Application Rate (gal/acre) | Weight Percent of SCYTHE |
|---|---|---|
| 3. SCYTHE Pelargonic Acid (water) | 100 | 2% |
| 4. SCYTHE Pelargonic Acid 11 N Oil | 10 | 80% (20% oil) |
| 5. SCYTHE Pelargonic Acid 11 N Oil | 10 | 40% (60% oil) |
| 6. SCYTHE Pelargonic Acid 11 N Oil | 10 | 20% (80% oil) |
| 7. SCYTHE Pelargonic Acid (neat) | 5 | 100% |
| 8. SCYTHE Pelargonic Acid | 5 | 80% 20% |

*SCYTHE is a commercial formulation of pelargonic acid.

Treatments were applied in a randomized complete block design with 2 replications per treatment. Experimental were located in San Pasqual Valley, Calif., and consisted of blocks of weeds 6 ft. wide×20 ft. long. Most of the weeds (Brassica sp., Amsinckia sp., and Chenopodium sp.) were 2–8 inches tall and evenly mixed. The application was made on April 10th and evaluated on April 11th. Conditions for the experiment were warm, dry and a little windy. The treatments were evaluated on a scale of 1–10 with a 10 representing complete burndown.

Sprays were applied with an N2 backpack sprayer. The boom had two overhead nozzles spaced 30 inches apart. Treatments were applied at 100 gallons/acre, 10 gallons/acre and 5 gallons/acre (gpa). Flat fan nozzles were used for all treatments: #8008 for 100 gpa, #8001 for 10 gpa and #8005 for 5 gpa. Gallonages were calculated by measuring the amount of water that flowed out of one nozzle at 50 psi. The results of the field test are listed below:

| Treatment Number | Evaluation Rating (Avg.) |
|---|---|
| 1 | 6.50 |
| 2 | 4.00 |
| 3 | 0.75 |
| 4 | 8.50 |
| 5 | 7.50 |
| 6 | 4.00 |
| 7 | 7.00 |
| 8 | 6.50 |

EXAMPLE 3

Effect of Volume on Water Based Fatty Acid Herbicidal Efficacy

A test was conducted to determine the effect of total application volume/acre on the control of barnyard grass with SCYTHE brand pelargonic fatty acid herbicide. Five different formulations were prepared to deliver 4 gallons of SCYTHE pelargonic acid herbicide per acre at application volumes of 40, 60, 80, 100 and 120 gallons/acre. Water was employed as the carrier. The results are shown in FIG. 1 and indicate that in a water based formulation the efficacy of pelargonic acid is dramatically reduced when the total volume applied per acre is reduced from 80–120 gallons down to 40 gallons.

In similar operations the various oils and fatty acid herbicides are combined in the various ratios and applied to unwanted vegetation without dilution in water. The oil based formulations are applied at low volume rates.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A method of applying a fatty acid herbicide to unwanted vegetation which comprises:

(a) providing an oil based C6–C20 fatty acid herbicide composition which comprises one or more fatty acid herbicides and at least 10 percent by weight of a compatible oil, and (b) applying the oil based composition to unwanted vegetation at an application rate of less than 25 gallons per acre and without diluting the composition in water.

2. The method, according to claim 1, wherein the fatty acid herbicide is comprised substantially of pelargonic acid or a salt or ester thereof.

3. The method, according to claim 1, wherein the oil is a triglyceride, a terpenoid or a paraffinic mineral oil.

4. The method, according to claim 1, wherein the fatty acid herbicide is pelargonic acid and the oil is a non-emulsified paraffinic oil.

5. The method, according to claim 4, wherein the weight ratio of pelargonic acid to oil is about 60–80:40–20 respectively.

6. A ready-to-use oil based fatty acid formulation consisting essentially of:

(a) a C6–C20 fatty acid or a mixture thereof, and (b) an oil that is compatible with the fatty acid herbicide.

7. The formulation, according to claim 6, wherein the fatty acid herbicide is pelargonic acid or a salt or ester thereof.

8. The formulation, according to claim 6, wherein the oil is a triglyceride, a terpenoid or a paraffinic mineral oil.

9. The formulation, according to claim 6, wherein the fatty acid is substantially pelargonic acid and the oil is a non-emulsified paraffinic oil.

10. The formulation, according to claim 9, wherein the pelargonic acid/oil weight ratio is about 60–80:40–20, respectively.

* * * * *